United States Patent [19]
Jacobs

[11] Patent Number: 4,801,807
[45] Date of Patent: Jan. 31, 1989

[54] SHIELD FOR PROTECTION OF A SLEEPING PERSON AGAINST HARMFUL RADIATION

[75] Inventor: Robert Jacobs, Nieuwegein, Netherlands

[73] Assignee: Olmac B.V., Nieuwegein, Netherlands

[21] Appl. No.: 864,797

[22] Filed: May 19, 1986

[30] Foreign Application Priority Data

May 18, 1985 [DE] Fed. Rep. of Germany ... 8514703[U]
Apr. 9, 1986 [DE] Fed. Rep. of Germany ....... 3611919

[51] Int. Cl.⁴ .............................................. G21F 3/00
[52] U.S. Cl. ................................. 250/515.1; 250/512.1
[58] Field of Search ............... 250/505.1, 515.1, 516.1, 250/517.1, 519.1; 5/1

[56] References Cited

U.S. PATENT DOCUMENTS 2,634,426  4/1953  Anderson ..................................... 5/1
2,857,525 10/1958  Ferdon ............................. 250/519.1

FOREIGN PATENT DOCUMENTS 0062063  4/1985  European Pat. Off. .
2360584  6/1975  Fed. Rep. of Germany ... 250/516.1
2716908 11/1977  Fed. Rep. of Germany ... 250/515.1
0025798  3/1978  Japan .................. 250/519.1
0216997 12/1983  Japan .................. 250/515.1
0766886  1/1957  United Kingdom ............. 250/515.1
2004406  3/1979  United Kingdom ............. 250/517.1

OTHER PUBLICATIONS

"Sleep Cager," The Washington Daily News, Jul. 8, 1953.

Primary Examiner—Bruce C. Anderson
Assistant Examiner—Paul A. Guss
Attorney, Agent, or Firm—Herbert Dubno

[57] ABSTRACT

A shield for protection from harmful radiation is provided, particularly for protecting a person lying in a bed from radiation originating in the ground. The shield comprises a plurality of thin walled overlapping platelets through which radiation can not pass which are positioned adjacent the bottom of the bed. Advantageously the platelets are connected with each other and with the mattress of the bed jointly by cord or pivot joint and are composed of lead and/or a barium containing compound such as barium sulfate or barium oxide. The shield can also be a fine powdered barium compound interspersed in the foam of the mattress.

13 Claims, 2 Drawing Sheets

SHIELD FOR PROTECTION OF A SLEEPING PERSON AGAINST HARMFUL RADIATION

FIELD OF THE INVENTION

My present invention relates to a shield for protection against harmful radiation and, more particularly, to a shield for protecting persons lying on a bed from radiation originating from the underlying ground.

BACKGROUND OF THE INVENTION

Radiation from the underlying ground can detrimentally affect both men and animals. Cases are known in which the same sickness has occurred in several successive generations of individuals when these individuals had their beds at the same location.

Research has shown that at some of these places underground water passed below the house and a remission of a budding illness of this type could be seen when the bed was moved.

Even the ancient Chinese noted the path of a subterranean water flow had a particular significance.

Where two such aquifers were on different levels a person sleeping above them can be subjected to comparatively high ground radiation levels. Injury to animals has also been established.

Apart from underground water as a radiation source, stone and underlying ground formations in the immediate vicinity of an underground water flow or at the intersection of underground water flows appears to intensify the surface radiation levels.

An especially great danger exists where individuals sleep since they spend a substantial amount of time there. It is theoretically possible, for shielding of this radiation, to provide an integrated layer of lead in the floor of the house although that is extremely expensive. Furthermore, regions of the house which do not require protection are needlessly shielded.

OBJECTS OF THE INVENTION

It is an object of my invention to provide a shield from harmful radiation.

It is a further object of my invention to provide a shield from radiation originating from the underlying ground in a house which is located where there is an especially high radiation level.

It is also an object of my invention to provide a shield in a bed which protects individuals sleeping or lying in bed from a high level of radiation originating from the underlying ground.

SUMMARY OF THE INVENTION

These objects and others which will become more readily apparent hereinafter are attained in accordance with my invention in a shield for protection against harmful radiation, particularly radiation originating from the surrounding earth, comprising a mattress and a material which serves as a radiation shield, such as lead, barium, or a compound thereof, extending along the mattress and in contact with the mattress body between the underlying ground and the individual. Specifically this material is provided at least along the underside of the mattress.

According to my invention a shield for protection against harmful radiation, particularly for protection of a individual lying on a bed from radiation originating from the ground, comprises a plurality of overlapping platelets each of which prevents the passage of the harmful radiation positioned in the vicinity of the underside of the mattress of the bed. Advantageously these platelets are thin walled and overlap only slightly.

This technique can be applied to the mattress or the entire bed without considerable expense, although the weight of the mattress is considerably increased by these platelets. Because of the thin walled structure and the fact that the radiation shielding layer is made up of small overlapping platelets the flexibility of the mattress is maintained. The platelets can also be attached to each other or laid over each other to form a single short mat. A loose attachment allows a desirable flexibility without gross position changes and thus platelet wandering is prevented. The platelets therefore prevent the radiation from the ground from acting on the body of an individual lying on the bed without impairing the comfort of the bed.

According to one embodiment of my invention the platelets are integrated in the mattress so that they cannot be detected from the outside. The individual platelets can thus be positioned in a continuous layer or in different layers as proves suitable. They can be applied from the inside to the sheathing of the mattress, woven in or otherwise attached providing that movability with respect to each other is maintained thereby rendering the mattress flexible. Furthermore, platelet size must also be chosen to provide this flexibility.

Too much overlap and thus too great a weight for the individual sheets is prevented when the platelets are attached to each other by cord or pivotal linkages or hinges, i.e. flexibly. Thus while preserving the movability required for flexibility, a continuous protective wall guarantees a shield against radiation from the ground.

An especially flexible and impervious shield results when the platelets are shaped like the shingles of a roof or like shakes or in a fishscale pattern. These structures have the further advantage that the individual platelets can advantageously be mechanically attached to one another to provide the required movability without permitting platelets to wander substantially from their average position.

To improve and facilitate the handling of this kind of shield the mobile platelets are fastened together into a mat and positioned as an independent element between the bed frame and the mattress. Thus it is also possible to shield only the upper part of the bed by such a mat according to where and how the radiation from the ground or other radiation occurs.

In another embodiment of my invention the individual platelets forming a continuous mat are each shrink wrapped in a plastic foil. This is a particularly easy way to manipulate the structure and provides a protection against the negative effects of some of the shield materials. The plastic foil is shrunk onto the platelets so that the required movability is preserved while a continuous shield is provided. By suitable choice of plastic foil, for example when a roughened material is chosen, it is guaranteed that the individual platelets will remain in place during use.

In a further embodiment of my invention the desired shielding effect is advantageously attained when the individual platelets are composed of lead and the edges on opposite sides of the platelets are folded corresponding to the adjacent platelet. This folded structure is such that the individual platelets are hooked together with each other and a structure of the continuous shield is attainable which provides a very flexible mat like a chain-linked skirt.

According to another embodiment of my invention the platelets are formed from flat linen or plastic sacks which are filled with fine grained or pulverized barium containing compounds, such as barium oxide or barium sulfate (baryte). These barium compounds can also be used in the form of platelets on which a plastic foil is shrunk.

However because of their brittleness these barium compounds can break forming gaps in the desired protective shield at critical locations. With fine grained or pulverized barium compounds a balancing and a shifting of the individual masses occurs inside the sacks so that a continuous shield is guaranteed. Also the barium compounds provide the necessary shield from radiation and have the advantage that the mattress in which they are employed can be washed.

My invention has the advantage that with comparatively little expense and effort a continuous protective shield for the body against radiation, particularly radiation from the ground, is attained without which either a change of domicile or sleeping location or a combination thereof is required for good health. The mattress or bed of this invention is easy to handle. Comfort is not impaired since the protective layer is an integral part of the mattress having the required flexibility to respond to varying loads.

Instead of the barium compound in pulverized form being sewn into sacks which are put into an additional lower layer or which are attached to a corresponding mattress, a further embodiment of my invention is possible. Therein a corresponding layer is formed comprising a mixture of fine grained barium compounds in a plastic foam or in a hardened foam advantageously polyurethane. Here the processing is particularly easy because the barium compound present in pulverized form can be mixed uniformly in the foam material. Thus, it can be applied in the foam material and is distributed very uniformly in it. The hardened foam can subsequently be cut into suitably thin layers of mattress dimensions which then are attached to the mattress or applied in a corresponding underlay beneath the mattress.

Thus, it is possible to form a protective shield without the danger of baryte powder running out of the mattress. The barium containing compound is distributed advantageously completely uniformly in the plastic foam so that the radiation is completely and totally stopped. Of course here too it is possible to cover and protect only those parts of the mattress which are endangered by radiation.

In another embodiment of my invention a thin layer of a fine grained barium compound and an adhesive mass or glue is applied to the mattress. Since it is naturally possible to apply this layer to the underside of the mattress in a suitably uniform mixture, it is possible to provide a reliable protective layer to protect against harmful radiation. With this embodiment there is assurance that the protection lasts because of the permanent attachment of the layer with the mattress or frame.

It is particularly advantageous when lead platelets are used in a thickness of 1 mm. The barium compound/adhesive mixture or barium compound/foam mixture has a thickness of 4 mm. When a suitable structure for the protective shield according to my invention is provided the penetration of ground-derived radioactivity is effectively completely halted.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
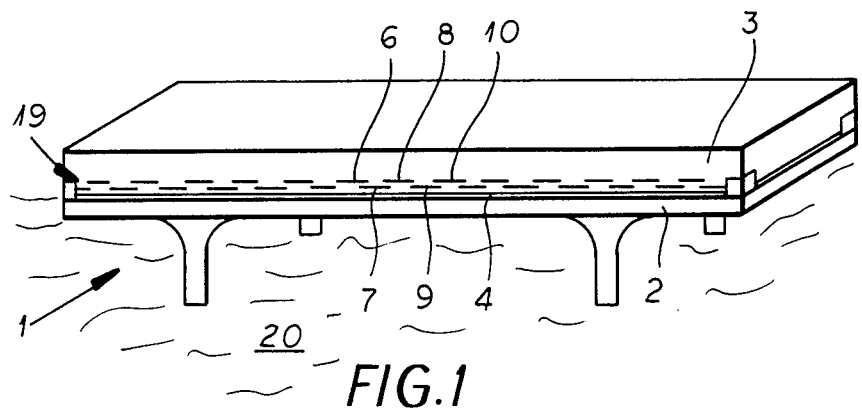
FIG. 1 is a schematic perspective view of a bed containing the radiation shield according to my invention.

FIG. 1 shows a simple bed 1 comprising a bed frame or pallet 2 and a mattress 3 lying on top of it. Adjacent the bottom 4 of the mattress 3, the platelets 6, 7, 8, 9 and 10 are integrated with the mattress 3.

These platelets form a shield 19 which radiation from the underlying ground 20 can not penetrate and which protects a person lying on the mattress 3.

Figure 2:
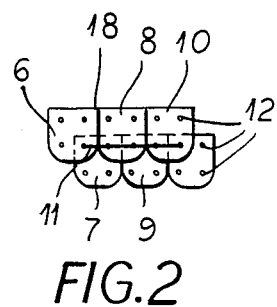
FIG. 2 is a top plan view of some of the platelets forming the radiation shield of FIG. 1.

The platelets 6, 7, 8, 9, 10 etc. then form as indicated in FIG. 2 a continuous mat 18 which is provided with an advantageous mobility or flexibility which allows it to adjust to the pressure resulting from an individual pressing down on the bed and the mat 18 forming the shield.

In the embodiment shown in FIG. 2 the individual platelets 6, 7, 8, 9 and 10 are Connected with each other by cord 11. The cord 11 is guided through holes 12 in the individual platelets, for example 6, 7, 8, 9, 10 etc. That results in the above mentioned advantageous flexibility or mobility of the individual platelets.

Figure 3:
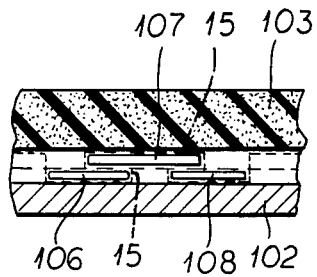
FIG. 3 is a side sectional view of a portion of another embodiment of the radiation shield according to my invention.

FIG. 3 shows another embodiment in which the individual platelets 106, 107, 108, etc., below the mattress 103 and on the pallet 102, are received in plastic foil 15 which does not restrict their mobility. In the embodiment of FIG. 3 a comparatively large overlap of the individual platelets 106, 107, 108, etc. is provided. This overlap can be considerably reduced because of the shrink-wrap plastic foil 15, so that the individual platelets which are adjacent one another can be frictionally connected or heat sealed together by the plastic foil 15.

Figure 4:
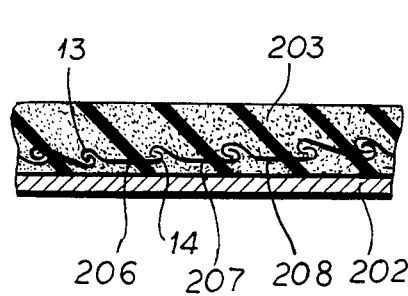
FIG. 4 is a side sectional view of a group of platelets from a further embodiment according to my invention showing how they are linked together.

FIG. 4 shows yet another embodiment in which the individual lead platelets 206, 207, 208, etc., embedded in the foam mattress 203 at its underside against the bed pallet 202, have edges 13 and 14 folded over in different directions on opposite sides of the platelets so that a pivotal or hinged linking of the platelets results.

Figure 5:
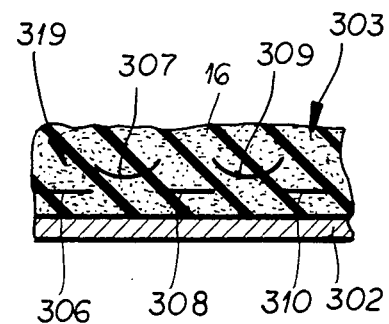
FIG. 5 is yet another cross sectional view of a mattress assembly with a radiation shield according to my invention showing how the platelets can be distributed through the foam of a mattress.

FIG. 5 shows an embodiment in which the plates 306, 308, 310 and/or 307, 309, etc. are mounted in different planes in a foam or plastic foam 16 forming the mattress 303 on the pallet 302. The platelets 307 and 309 which are shown with a curved cross section can also be inverted. These platelets are scattered or dispersed throughout the foam 16 but in such a way as to provide complete coverage and thus an effective shield 319 against radiation.

Figure 6:
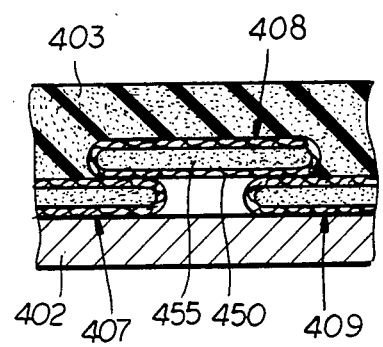
FIGS. 6, 7, and 8 show alternative embodiments of the radiation shield according to my invention in respective cross sectional views.

FIG. 6 shows an embodiment in which each of the platelets 406, 407, 408, 409, below the mattress 403 and above the pallet 402, is formed from a flat linen or plastic bag 450 which is filled with a fine grained or pulverized barium containing compound 455.

Figure 7:
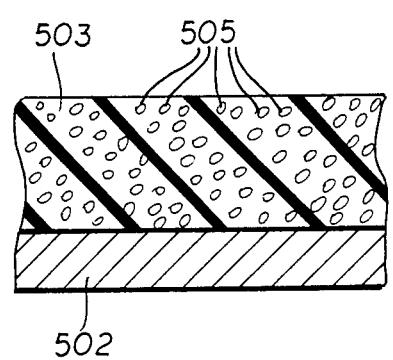

In another embodiment shown in FIG. 7 a fine grained or pulverized barium compound 505 is mixed with a foam material 507 in the mattress 503 on a frame 502. The foam 507 is advantageously a relatively stiff polyurethane foam.

Figure 8:
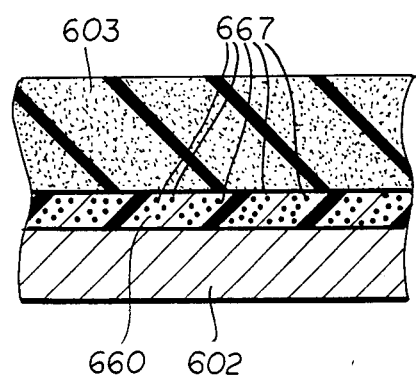

FIG. 8 shows an embodiment in which a thin layer 660 composed of fine grained barium compound 667 and an adhesive substance 668 are applied to the mattress 603.

I claim:

1. A shield for protection against harmful radioactive decay products such as from uranium or radon, particularly for protection of an individual from said radioactive decay products present within the ground, comprising:
   a mattress which is part of a bed upon which said individual sleeps and which has an upper part forming a sleeping surface; and
   a plurality of overlapping elements at least along an underside of said mattress preventing the passage of said radiation to an individual lying on said mattress, said elements being formed from a material selected from lead, barium and compounds thereof, said elements being thin wall platelets and overlapping only slightly.

2. A shield for protection against said harmful radiation according to claim 1 wherein said platelets are integrated into said mattress.

3. A shield for protection against said harmful radiation according to claim 1 wherein said platelets are connected with each other flexibly.

4. A shield for protection against said harmful radiation according to claim 1 wherein said platelets are disposed in a fishscale or shingle pattern.

5. A shield for protection against said harmful radiation according to claim 1 wherein said platelets are connected with each other so as to be movable and are fastened together to form a continuous self-supporting mat, said mat being placed on top of a bed frame which carries said mattress.

6. A shield for protection against said harmful radiation according to claim 1 in which said platelets are shrink wrapped in a plastic foil.

7. A shield for protection against said harmful radiation according to claim 1 in which said platelets are composed of lead and the edges of said platelets are folded to engage those of adjacent platelets.

8. A shield for protection against said harmful radiation according to claim 1 wherein said platelets are approximately 1 mm thick.

9. A shield for protection against harmful radioactive decay products such as from uranium or radon, particularly for protection of an individual from said radioactive decay products present within the ground, comprising:
   a mattress which is part of a bed upon which said individual sleeps and which has an upper part forming a sleeping surface; and
   a plurality of overlapping elements at least along an underside of said mattress preventing the passage of said radiation to an individual lying on said mattress, said elements being formed from a material selected from lead, barium and compounds thereof, each of said elements being formed from a flat linen or plastic bag which is filled with a fine grained barium compound.

10. A shield for protection against harmful radioactive decay products such as from uranium or radon, particularly for protection of an individual from said radioactive decay products present within the ground, comprising:
    a mattress which is part of a bed upon which said individual sleeps and which has an upper part forming a sleeping surface; and
    a plurality of overlapping elements at least along an underside of said mattress preventing the passage of said radiation to an individual lying on said mattress, said elements being formed from a material selected from lead, barium and compounds thereof, a fine grained or pulverized barium compound being mixed with a foam material in said mattress.

11. A shield for protection against said harmful radiation according to claim 10 in which said foam advantageously comprises a hardened polyurethane foam.

12. A shield for protection against harmful radioactive decay products such as from uranium or radon, particularly for protection of an individual from said radioactive decay products present within the ground, comprising:
    a mattress which is part of a bed upon which said individual sleeps and which has an upper part forming a sleeping surface; and
    a plurality of overlapping elements at least along an underside of said mattress preventing the passage of said radiation to an individual lying on said mattress, said elements being formed from a material selected from lead, barium and compounds thereof, a thin layer composed of a fine grained barium compound and an adhesive substance being applied to said mattress.

13. A shield for protection against said harmful radiation according to claim 12 wherein said layer of said barium compound and said adhesive substance has a thickness of at least 4 mm.

* * * * *